(12) United States Patent
Biel et al.

(10) Patent No.: US 11,974,642 B2
(45) Date of Patent: May 7, 2024

(54) LENS CARE CONTAINER

(71) Applicant: ALCON INC., Fribourg (CH)

(72) Inventors: Roger Biel, Aschaffenburg (DE);
Matthias Schwab, Amorbach (DE);
Justyna Justynska-Reimann,
Aschaffenburg (DE)

(73) Assignee: Alcon Inc., Fribourg (CH)

( * ) Notice: Subject to any disclaimer, the term of this patent is extended or adjusted under 35 U.S.C. 154(b) by 413 days.

(21) Appl. No.: 17/292,368

(22) PCT Filed: Nov. 8, 2019

(86) PCT No.: PCT/IB2019/059623
§ 371 (c)(1),
(2) Date: May 7, 2021

(87) PCT Pub. No.: WO2020/095267
PCT Pub. Date: May 14, 2020

(65) Prior Publication Data
US 2022/0000231 A1    Jan. 6, 2022

Related U.S. Application Data

(60) Provisional application No. 62/757,850, filed on Nov. 9, 2018.

(51) Int. Cl.
*A45C 11/00* (2006.01)
*A45C 15/00* (2006.01)
*A61L 12/08* (2006.01)

(52) U.S. Cl.
CPC ............ *A45C 11/005* (2013.01); *A45C 15/00* (2013.01); *A61L 12/086* (2013.01)

(58) Field of Classification Search
None
See application file for complete search history.

(56) References Cited

U.S. PATENT DOCUMENTS 5,099,987 A * 3/1992 Bieri .................... A45C 11/005
220/663
5,173,738 A * 12/1992 Bieri .................... A61F 9/0061
356/124

(Continued)

FOREIGN PATENT DOCUMENTS

WO    2013083993 A1    6/2013
WO    2013119757 A1    8/2013

OTHER PUBLICATIONS

Forschungsvorhaben "PRINTS", Gedruckte Nanomaterialien für die Mikrosensorik, Projektlaufzeit Apr. 1, 2011-Sep. 30, 2014', available at the TIB Leibniz-Informationszentrum Technik und Naturwissenschaften, Universitäts-bibliothek, Hannover, Bundesrepublik Deutschland. Research_project_PRINTS (Nanomaterial for microsensors—main part machine translation).

*Primary Examiner* — Fekadeselassie Girma
(74) *Attorney, Agent, or Firm* — Sheng-Hsin Hu

(57) ABSTRACT

A lens care container (1), in particular for contact lenses such as hard or soft contact lenses, comprises:
a receptacle (2) for receiving a lens and a lens care liquid,
a cap (3) configured to be attached to the receptacle (2) to close the receptacle (2),
a sensor (5) configured to indicate an actual loading of the container (1) with germs or configured to indicate a pH value of the lens care liquid in the receptacle (2).
The sensor (5) is arranged in the receptacle (2) when the cap (3) is attached to the receptacle (2).

5 Claims, 1 Drawing Sheet

(56) References Cited

U.S. PATENT DOCUMENTS

Figure 1:
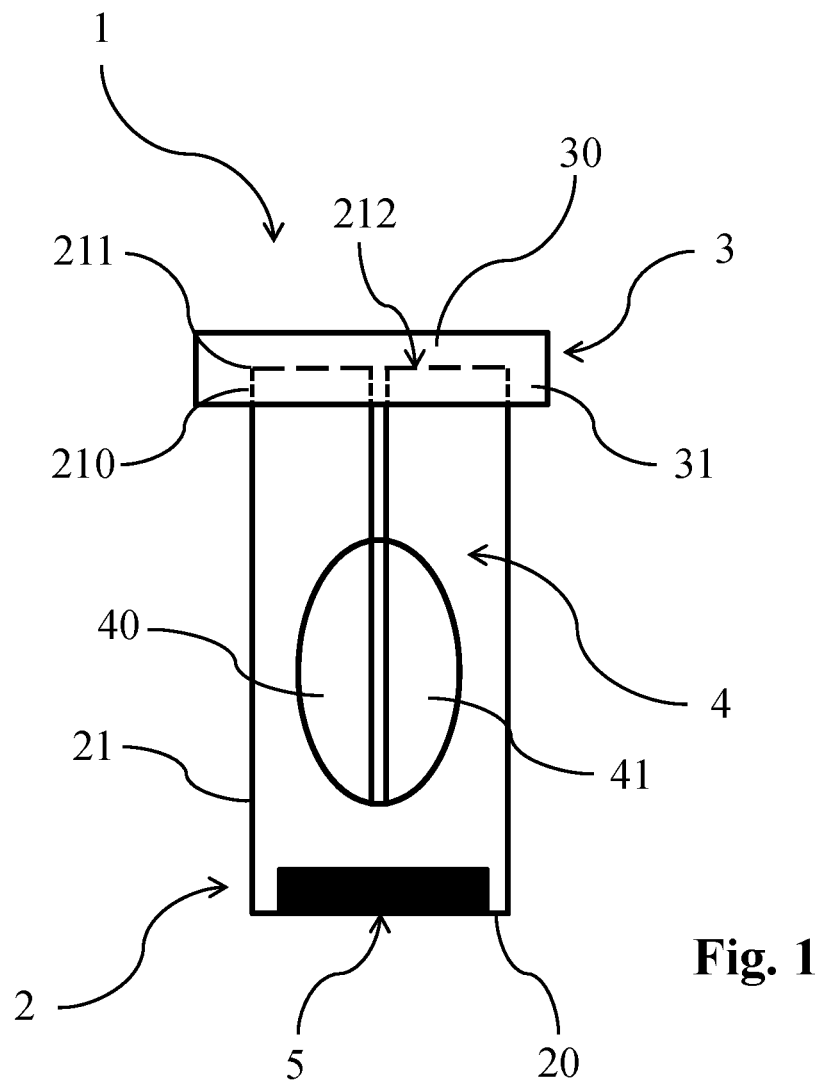

| | | | | |
|---|---|---|---|---|
| 5,699,900 A * | 12/1997 | Artis | ................ | A45C 11/005 |
| | | | | 206/459.1 |
| 8,158,961 B2 * | 4/2012 | Merkle | ............. | A61L 12/063 |
| | | | | 250/365 |
| 9,176,332 B1 * | 11/2015 | Etzkorn | ................ | G02C 7/04 |
| 9,217,881 B2 * | 12/2015 | Pugh | .................... | G02C 7/04 |
| 9,332,935 B2 * | 5/2016 | Etzkorn | ............. | A61B 5/682 |
| 10,288,909 B1 * | 5/2019 | Youssef | ................ | H04B 1/48 |
| 10,413,182 B2 * | 9/2019 | Flitsch | ............ | G06Q 30/0261 |
| 10,705,352 B2 * | 7/2020 | Greeson | ............ | G02C 13/008 |
| 2002/0125436 A1 * | 9/2002 | Muller | ............. | B65B 25/008 |
| | | | | 250/341.1 |
| 2011/0084834 A1 * | 4/2011 | Sabeta | ............. | G06K 19/077 |
| | | | | 340/540 |
| 2018/0184904 A1 * | 7/2018 | Kuniavsky | ....... | A61B 5/14532 |

* cited by examiner

LENS CARE CONTAINER

The present invention relates to a lens care container.

In the field of contact lenses it is differentiated between single use contact lenses, i.e. contact lenses which are worn only once and are then disposed of, and multiple use contact lenses which are worn multiple times. Single use contact lenses are mass manufactured in highly automated manufacturing lines and are comparatively cheap. It goes without saying that for single use contact lenses no lens care is required as these lenses are disposed of after being worn. However, single use contact lenses are available only for certain types of geometries of the cornea of the eye of the wearer and for certain ranges of visual corrections. The rarer the geometry of the cornea of the eye of the wearer or the rarer a required visual correction, the less likely it is that single use contact lenses are available for such wearer.

Contact lenses which are worn multiple times need to be disinfected and cleaned after being worn. Typically, contact lenses which are worn multiple times are more expensive as regards manufacturing costs. Also, the materials such contact lenses are made of need to be different since these contact lenses need lens care, that is to say the contact lenses need to be cleaned and disinfected before being worn again, and/or need to be placed in a storing liquid for being stored.

While lens care containers of many different types and shapes are known, two types are particularly widespread. The first type is a flat container comprising two receptacles, one at each end of the container, and the receptacles are connected to each other by a web. Each of the receptacles comprises a bottom and a circumferentially running receptacle sidewall extending upwardly from the outer end of the bottom, however, only for a short distance to allow an outer thread to be provided on the outer surface of the receptacle sidewall. The lens care container further comprises two caps, one for each receptacle. Each cap comprises a lid and a downwardly extending cap sidewall which is provided on its inner wall with an inner thread. For cleaning, disinfecting or storing the contact lenses, the lenses are placed into the receptacles, one lens in each receptacle, and a lens care liquid is filled into the respective receptacle. Thereafter, the caps are screwed onto the receptacles, and the contact lenses are allowed to be disinfected, cleaned or stored in the container.

The second type of container comprises only one receptacle. This receptacle comprises a bottom and a circumferentially running receptacle sidewall extending upwardly from a radial outer end of the bottom, so that the receptacle looks like a small slim cup. At an upper end portion the receptacle sidewall terminates in an upper rim that surrounds a top opening of the receptacle. In the upper end portion of the receptacle sidewall, the receptacle sidewall is provided with an outer thread on its outer surface. The associated cap comprises a lid and a circumferentially running cap sidewall extending downwardly from the lid. On an inner wall the cap sidewall comprises and inner thread corresponding to the outer thread on the outer surface of the receptacle sidewall. A holder is attached to the lid of the cap and projects downwardly from the lid. The holder comprises two baskets for accommodating and holding the contact lenses, one in each basket. For cleaning, disinfecting or storing the contact lenses, a lens care liquid is filled into the receptacle, and the cap with the holder and the baskets accommodating the contact lenses is then screwed onto the receptacle, and the contact lenses are allowed to be cleaned, disinfected or stored in the container. Typically the receptacle is made of a transparent plastic material allowing a view to the interior of the receptacle where the contact lenses are held in the lens care liquid.

Lens care containers are made for repeated use, too, before being disposed of. The manufacturers of lens care containers typically specify a maximum duration of use (e.g. some weeks), and then they specify that the lens care container be disposed of. One reason why the manufacturers specify such maximum duration of use is that germs may settle over time on an inner wall of the receptacle, on the cap or on the holder attached to the cap, and this in turn involves the risk that such germs be transferred to the contact lenses stored in the lens care container. Also, in case the lens care container is exposed to an environment in which adverse conditions exist, for example an unclean environment, such risk of germs being transferred to the contact lenses may exist. However, placing contact lenses loaded with germs onto the eye may lead to severe health consequences.

Therefore, it is one object of the invention to suggest a lens care container that allows to identify when the container is no longer acceptable for use due to involving the risk of transfer of germs.

Also, taking the contact lens from the lens care container at a time when the cleaning and disinfecting process is not yet completed so that the lens care liquid has not yet been neutralized would involve the risk of causing any reactions (e.g. inflammatory reactions) of the eye due to incomplete neutralization of the lens care liquid.

Therefore, it is another object of the invention to suggest a lens care container that allows the user to identify whether or not the disinfecting and cleaning process is completed.

These objects are achieved by a lens care container as it is specified by the independent claims. Additional advantageous aspects of the lens care container according to the invention are the subject of the dependent claims.

The lens care container according to the invention, in particular for contact lenses such as hard or soft contact lenses, comprises
  a receptacle for receiving a lens and a lens care liquid,
  a cap configured to be attached to the receptacle to close the receptacle,
  a sensor configured to indicate an actual loading of the container with germs or configured to indicate a pH value of the lens care liquid in the receptacle, the sensor being arranged in the receptacle when the cap is attached to the receptacle.

According to one aspect of the lens care container according to the invention, the sensor is a printable bioelectronic sensor. The term 'bioelectronic' in this regard means that it is an electronic sensor that is capable of measuring a biologically relevant value (here: the loading of the container with germs or the pH value). The term 'printable' in this regard means that the sensors are manufactured using printing techniques. The sensor may be directly printed to a wall of the container or may be printed on a foil which is then attached to a surface of the container.

According to a further advantageous aspect of the lens care container according to the invention, the receptacle comprises
  a bottom
  a circumferentially running receptacle sidewall extending upwardly from a radial outer end of the bottom and having an upper end portion that terminates in an upper rim surrounding a top opening of the receptacle,
  an outer thread arranged in the upper portion of the receptacle sidewall on an outer surface thereof.

The cap comprises
a lid
a circumferentially running cap sidewall extending downwardly from the lid,
an inner thread arranged on an inner wall of the cap sidewall,
wherein the outer and inner threads are configured to allow for screwing the cap onto the receptacle to close the top opening, thereby closing the container.

According to one aspect of the lens care container according to the invention, the sensor is arranged on an inner wall of the bottom of the receptacle.

According to another aspect of the lens care container according to the invention, the sensor is arranged on an inner wall of the receptacle sidewall.

According to a further aspect of the lens care container according to the invention, the container further comprises a holder attached to the lid of the cap and projecting downwardly from the lid. The holder comprises at least one basket for accommodating and holding the lens in the receptacle when the cap is screwed onto the receptacle.

According to still another aspect of the lens care container according to the invention, the sensor is arranged on the holder.

Of course it is possible to have more than one sensor, so that combinations of the arrangements of the sensor on the bottom of the receptacle, on an inner wall of the receptacle sidewall and on the holder are possible.

Providing the lens care container with a sensor which is configured to indicate an actual loading of the receptacle with germs allows to indicate to the user that the lens care container should not be used any longer but should be disposed of. A sensor providing an indication of the pH value of the lens are liquid in the receptacle allows the user to determine whether the cleaning and disinfecting process is complete and the lens care liquid has been neutralized again, so that the contact lens can be taken out of the container and be placed onto the eye. Of course, it is also conceived to use one or more sensors that indicate both the loading of the receptacle with germs and the pH value of the lens care liqud (and possibly also additional biologically relevant parameters). Such sensor or sensors could be arranged anywhere in the receptacle as long as it is/they are capable of generating a signal representative of the loading of germs in the receptacle or of the pH value of the lens care liquid (or possibly of additional biologically relevant parameters). Particularly suitable sensors are printable bioelectronic sensors, and are described, for example, in the report 'Forschungsvorhaben "PRINTS", Gedruckte Nanomaterialien für die Mikrosensorik, Projektlaufzeit 1 Apr. 2011-30 Sep. 2014', available at the TIB Leibniz-lnformationszentrum Technik and Naturwissenchaften, Universitätsbibliothek, Hannover, Bundesrepublik Deutschland. Suitable sensors are described in chapter 1, in particular in subchapter 1.11. Such sensors are free of any cables and do not need any power sources like batteries, they may simply comprise a kind of an energy storage that can be inductively charged, for example. Therefore, the sensor can be easily arranged at any desired location in the receptacle, for example on an inner wall of the receptacle bottom, on an inner wall of the receptacle sidewall or on the holder that is attached to the cap and that comprises the basket for accommodating the lenses. Read-out of the sensor can be achieved, for example, using Bluetooth technology or any other suitable wireless technology. Also, read-out of the sensor could be performed using NFC technologies (Near Field Communication technologies based on RFID-technology, Radio Frequency IDentification) available for smartphones, for example. The user may thus easily identify when the lens care container should not be used anymore but should be disposed of. Also, one advantage of printable bioelectronics sensors is that they are easy and cheap to manufacture so that the can be used in lens care containers which are mass manufactured.

Figure 2:
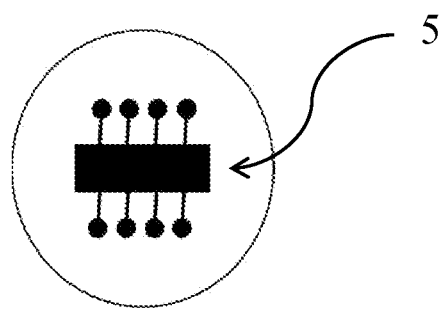

Further advantageous aspects will become apparent from the following description of embodiments of the invention with the aid of the drawings in which:

FIG. 1 shows an embodiment of a lens care container according to the invention, with a printable bioelectronics sensor arranged on the bottom of the container; and FIG. 2 shows an embodiment of a printable bioelectronic sensor of FIG. 1.

As used in the specification including the appended claims, the singular forms 'a', 'an', and 'the' include the plural, unless the context explicitly dictates otherwise. When using the term 'about' with reference to a particular numerical value or a range of values, this is to be understood in the sense that the particular numerical value referred to in connection with the term 'about' is included and is explicitly disclosed, unless the context clearly dictates otherwise. For example, if a range of 'about' numerical value a to 'about' numerical value b is disclosed, this is to be understood to include and explicitly disclose a range of numerical value a to numerical value b. Also, whenever features are combined with the term 'or', the term 'or' is to be understood to also include 'and' unless it is evident from the specification that the term 'or' must be understood as being exclusive.

FIG. 1 shows an embodiment of a lens care container according to the invention. Lens care container 1 comprises a receptacle 2 having a bottom 20 and a circumferentially running receptacle sidewall 21 extending upwardly from a radial outer end of bottom 20. Receptacle sidewall 21 has an upper end portion 210 on the outer surface of which is arranged an outer thread (not visible in FIG. 1). Upper end portion 210 of sidewall 21 terminates in an upper rim 211 that surrounds a top opening 212 of receptacle 2. Lens care container 1 further comprises a cap 3 that comprises a lid 30 and a circumferentially running cap sidewall 31 extending downwardly from lid 30 at a radial outer end of lid 30. An inner thread (not shown) is provided on an inner wall of the cap sidewall 31. The outer and inner threads correspond to each other so that they allow cap 3 to be screwed onto receptacle 2 to close container 1, and to be unscrewed from receptacle 2 to open container 1. A holder 4 is attached to lid 30 of cap 3 and comprises two baskets 40, 41 each for accommodating a contact lens and holding the contact lens in the receptacle 2 when cap 3 is screwed onto receptacle 2.

For performing lens care, a lens care liquid is filled through top opening 212 into receptacle 2, and the contact lenses to be cleaned, disinfected or stored (or all of these) are placed into baskets 40, 41 of lens holder 4. Cap 3 to which holder 4 is attached is then screwed onto receptacle 2 whereby the container 1 is closed and the lenses are held in the lens care liquid that has been filled into receptacle 2. After a predetermined time the cap is unscrewed, the contact lenses are taken out of the baskets 40, 41 and may then be worn.

So far container 1 is well-known in the art. However, when being used over extended periods of time or in an adverse environment (e.g. in an unclean environment) it is possible that container 1 (or to be more precise: the parts of container 1) is loaded with germs. Such germs may then be inadvertently transferred to the contact lenses. This is to be avoided since placing contact lenses loaded with germs onto the eye may lead to severe health consequences for the wearer.

In order to identify that container 1 is no longer acceptable for use and should be disposed of (i.e. it is loaded with germs to an extent that is not tolerable), container 1 comprises a sensor 5 which is configured to indicate an actual loading of the container (here: the receptacle 2) with germs. In the embodiment shown in FIG. 1 sensor 5 is arranged on an inner wall of bottom 20 and is shown exaggeratedly large, and is shown in a view from above in FIG. 2. Alternatively or in addition, the sensor 5 (or additional sensors) may be arranged on an inner wall of receptacle sidewall 21, on holder 4, or on any other suitable location (e.g. on an inner wall of lid 30 of cap 3).

As mentioned already, suitable sensors are printable bioelectronic sensors, as these are described in the report 'Forschungsvorhaben "PRINTS", Gedruckte Nanomaterialien für die Mikrosensorik, Projektlaufzeit 1 Apr. 2011-30 Sep. 2014', available at the TIB Leibniz-Informationszentrum Technik and Naturwissenschaften, Universitätsbibliothek, Hannover, Bundesrepublik Deutschland (see above). Such sensors are free of any cables and do not need any power sources like batteries, they may simply comprise a kind of an energy storage that can be inductively charged, for example. Therefore, sensor 5 can be easily arranged at any desired location in the receptacle, for example at the locations mentioned above. Read-out of the sensor can be achieved, for example, using Bluetooth technology or any other suitable wireless technology. Also, read-out of the sensor could be performed using NFC technologies (Near Field Communication technologies based on RFID-technology, Radio Frequency IDentification) available for smartphones, for example. The user may thus easily identify when lens care container 1 should not be used anymore but should be disposed of. For example, a suitable application ('App') on a smart-phone may simply provide a message to the user that the container should be disposed of.

The lens care container 1 according to the invention is simple in construction and is easy, reliably and cheap to manufacture since the costs for printable bioelectronics sensors 5 are low. Sensor 5 may be directly printed onto a wall of container 1 (in the embodiment shown onto an inner wall of bottom 20 of receptacle 2), or may be printed onto a thin foil which is then attached to a wall of container 1 (in the embodiment shown onto the inner wall of bottom 20), to the cap 3 or to the holder 4. At the same time, sensor 5 allows to reliably detect when a container is no longer acceptable for use (due to being loaded with germs), it does not need a battery, and the read-out can be performed with conventional means such as a smart-phone or any other suitable wireless read-out means using techniques (NFC, RFID) which are readily available on the market and convenient to use.

The lens care container according to the invention has been described with the aid of an embodiment. However, the invention is not limited to the described embodiment, but rather numerous changes and modifications are possible without departing from the teaching underlying the instant invention. For example, the invention also relates to lens care containers having two receptacles onto the sidewall of each of which is screwed a separate cap (as discussed in the introductory portion). In such case, the sensor could be provided either on the bottom, on the sidewall or on an inner surface of the lid of the cap, or combinations thereof. Therefore, the scope of protection is defined by the appended claims.

The invention claimed is:

1. Lens care container (1) for contact lenses, the container (1) comprising:
   a receptacle (2) for receiving a lens and a lens care liquid,
   a cap (3) configured to be attached to the receptacle (2) to close the receptacle (2),
   a sensor (5) configured to indicate an actual loading of the container (1) with germs or configured to indicate a pH value of the lens care liquid in the receptacle (2),
   wherein the sensor (5) is arranged in the receptacle (2) when the cap (3) is attached to the receptacle (2),
   a holder (4) attached to the lid (30) of the cap (3) and projecting downwardly from the lid (30), the holder (4) comprising two baskets (40, 41) for accommodating and holding the lens, one in each basket, in the receptacle (2) when the cap (3) is screwed onto the receptacle (2),
   wherein the sensor (5) is a printable bioelectronic sensor.

2. Lens care container according to claim 1, wherein the receptacle (2) comprises
   a bottom (20)
   a circumferentially running receptacle sidewall (21) extending upwardly from a radial outer end of the bottom (20) and having an upper end portion (210) that terminates in an upper rim (211) surrounding a top opening (212) of the receptacle (2),
   an outer thread arranged in the upper portion (210) of the receptacle sidewall (21) on an outer surface thereof,
   wherein the cap (3) comprises
   a lid (30)
   a circumferentially running cap sidewall (31) extending downwardly from the lid (30),
   an inner thread arranged on an inner wall of the cap sidewall (31),
   wherein the outer and inner threads are configured to allow for screwing the cap (3) onto the receptacle (2) to close the top opening (212), thereby closing the container (1).

3. Lens care container according to claim 2, wherein the sensor (5) is arranged on an inner wall of the bottom (20) of the receptacle (2).

4. Lens care container according to claim 2, wherein the sensor (5) is arranged on an inner wall of the receptacle sidewall (21).

5. Lens care container according to claim 2, wherein the sensor (5) is arranged on the holder (4).

* * * * *